(12) United States Patent
Lee

(10) Patent No.: US 8,914,120 B2
(45) Date of Patent: Dec. 16, 2014

(54) METHOD FOR TREATING DEPRESSION BY INDIRECTLY STIMULATING RAPHE NUCLEI

(71) Applicant: Boston Scientific Neuromodulation Corporation, Valencia, CA (US)

(72) Inventor: Dongchul Lee, Agua Dulce, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

(21) Appl. No.: 14/037,771

(22) Filed: Sep. 26, 2013

(65) Prior Publication Data

US 2014/0094886 A1      Apr. 3, 2014

Related U.S. Application Data

(60) Provisional application No. 61/708,512, filed on Oct. 1, 2012.

(51) Int. Cl.
*A61N 1/36* (2006.01)
*A61N 1/05* (2006.01)

(52) U.S. Cl.
CPC .......... *A61N 1/0551* (2013.01); *A61N 1/36057* (2013.01); *A61N 1/36096* (2013.01); *A61N 1/36157* (2013.01); *A61N 1/36171* (2013.01); *A61N 1/36175* (2013.01)
USPC ......................................................... 607/45

(58) Field of Classification Search
None
See application file for complete search history.

(56) References Cited

U.S. PATENT DOCUMENTS

| 6,895,280 B2 | 5/2005 | Meadows et al. |
| 7,650,184 B2 | 1/2010 | Walter |
| 8,019,439 B2 | 9/2011 | Kuzma et al. |
| 2006/0074450 A1* | 4/2006 | Boveja et al. ................... 607/2 |
| 2007/0067004 A1* | 3/2007 | Boveja et al. ................... 607/45 |
| 2007/0150036 A1 | 6/2007 | Anderson |
| 2007/0168004 A1 | 7/2007 | Walter |
| 2007/0168007 A1 | 7/2007 | Kuzma et al. |
| 2010/0249859 A1* | 9/2010 | DiLorenzo ....................... 607/2 |

OTHER PUBLICATIONS

Dafny, Nachum. "Anatomy of the Spinal Cord (Section 2, Chapter 3)". Neuroscience Online: An Electronic Textbook for the Neurosciences. Department of Neurobiology and Anatomy, The UT Medical School at Houston. 1987. Web. Jun. 6, 2014. <http://neuroscience.uth.tmc.edu/s2/chapter03.html>.*
Klop, E.M. et al., Direct Projections from the sacral spinal cord to the medial preoptic area in cat and guinea pig, Neuroscience, Dec. 2009; 164(4): 1732-43.

* cited by examiner

*Primary Examiner* — Kennedy Schaetzle
*Assistant Examiner* — Erica Lee
(74) *Attorney, Agent, or Firm* — Vista IP Law Group

(57) ABSTRACT

A method for treating a patient suffering from depression, the method including applying electrical stimulation energy to afferent nerve fibers leading to the medial preoptic region of the hypothalamus of the patient, thereby activating serotonin in the raphe nuclei to treat depression.

5 Claims, 8 Drawing Sheets

METHOD FOR TREATING DEPRESSION BY INDIRECTLY STIMULATING RAPHE NUCLEI

RELATED APPLICATION DATA

The present application claims the benefit under 35 U.S.C. §119 to U.S. provisional patent application Ser. No. 61/708,512, filed Oct. 1, 2012. The foregoing application is hereby incorporated by reference into the present application in its entirety.

FIELD OF THE INVENTION

The present invention relates to tissue stimulation systems, and more particularly, to spinal cord stimulation systems.

BACKGROUND OF THE INVENTION

Implantable neurostimulation systems have proven therapeutic in a wide variety of diseases and disorders. For example, Spinal Cord Stimulation (SCS) techniques, which directly stimulate the spinal cord tissue of the patient, have long been accepted as a therapeutic modality for the treatment of chronic neuropathic pain syndromes, and the application of spinal cord stimulation has expanded to include additional applications, such as angina pectoralis, peripheral vascular disease, and incontinence, among others. Spinal cord stimulation is also a promising option for patients suffering from motor disorders, such as Parkinson's Disease, Dystonia and essential tremor.

An implantable SCS system typically includes one or more electrode-carrying stimulation leads, which are implanted at a stimulation site in proximity to the spinal cord tissue of the patient, and a neurostimulator implanted remotely from the stimulation site, but coupled either directly to the stimulation lead(s) or indirectly to the stimulation lead(s) via a lead extension. The neurostimulation system may further include a handheld patient programmer to remotely instruct the neurostimulator to generate electrical stimulation pulses in accordance with selected stimulation parameters. The handheld programmer may, itself, be programmed by a technician attending the patient, for example, by using a Clinician's Programmer (CP), which typically includes a general purpose computer, such as a laptop, with a programming software package installed thereon.

Thus, programmed electrical pulses can be delivered from the neurostimulator to the stimulation lead(s) to stimulate or activate a volume of the spinal cord tissue. In particular, electrical stimulation energy conveyed to the electrodes creates an electrical field, which, when strong enough, depolarizes (or "stimulates") the neural fibers within the spinal cord beyond a threshold level, thereby inducing the firing of action potentials (APs) that propagate along the neural fibers to provide the desired efficacious therapy to the patient.

Depression is a medical condition affecting millions of persons worldwide. Treatment for depression has primarily focused on pharmaceutical approaches, and success has been achieved by employing selective serotonin reuptake inhibitors (SSRI) and tricyclic antidepressants. These approaches all focus on the generation and metabolism of serotonin, which is released from the raphe nuclei, located in the midbrain. A number of pharmaceutical compounds are available, but those compounds differ widely in their effectiveness and side effects, and accurately determining which compound fits a particular patient has proved difficult. Thus, there remains a continuing need for treatment approaches to depression that overcome the inherent drawbacks of pharmaceuticals.

SUMMARY OF THE INVENTION

In accordance with the present inventions, a method for treating a patient from depression is provided. The method includes applying electrical stimulation energy to afferent nerve fibers leading to the medial preoptic region of the hypothalamus of the patient, thereby activating serotonin in the raphe nuclei to treat depression. In one method, the electrical stimulation energy is epidurally applied to the afferent nerve fibers. In another method, the afferent nerve fibers are a dorsal root (DR). In still another method, the afferent nerve fibers are within laminae VI-X of the spinal cord. In yet another method, the electrical stimulation energy is applied to the afferent nerve fibers at a spinal level in the range of S1-S3. The electrical stimulation energy may be epidurally applied to the afferent nerve fibers, e.g., by at least one electrode implanted within the dorsal-lateral quadrant of an epidural space of the patient.

Other and further aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present invention are obtained, a more particular description of the present invention briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION

Figure 1:
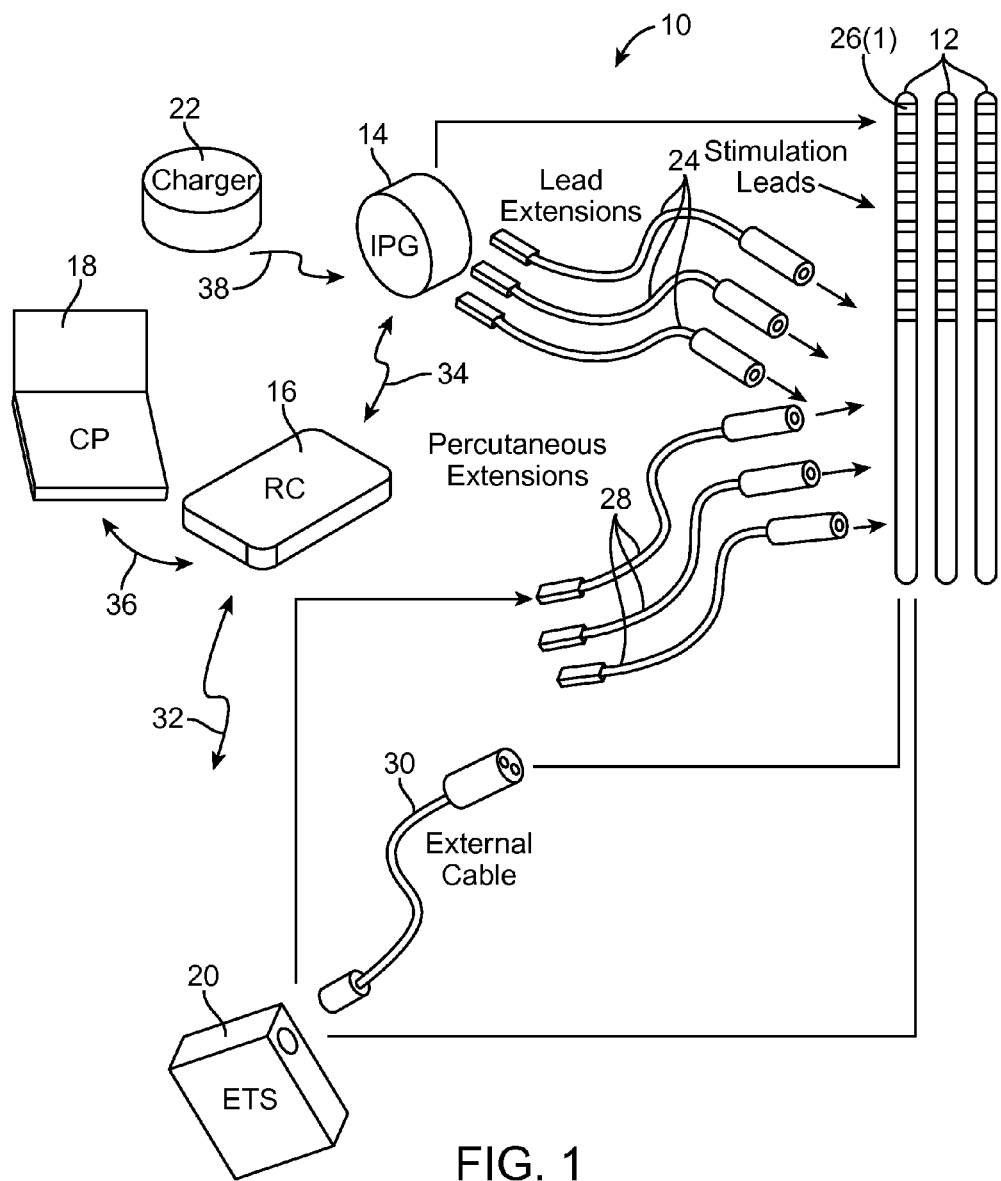
FIG. 1 is a plan view of a Spinal Cord Stimulation (SCS) system constructed in accordance with one embodiment of the present inventions.

Turning first to FIG. 1, an exemplary SCS system 10 generally comprises a plurality of stimulation leads 12 (in this case, three), an implantable pulse generator (IPG) 14 (or alternatively RF receiver-stimulator), an external remote control (RC) 16, a Clinician's Programmer (CP) 18, an External Trial Stimulator (ETS) 20, and an external charger 22.

The IPG 14 is physically connected via one or more lead extensions 24 to the stimulation leads 12, which carry a plurality of electrodes 26 arranged in an array. The stimulation leads 12 are illustrated as percutaneous leads in FIG. 1, although as will be described in further detail below, a surgical paddle lead can be used in place of the percutaneous leads. As will also be described in further detail below, the IPG 14 includes pulse generation circuitry that delivers electrical stimulation energy in the form of a pulsed electrical waveform (i.e., a temporal series of electrical pulses) to the electrode array 26 in accordance with a set of stimulation parameters.

The ETS 20 may also be physically connected via the percutaneous lead extensions 28 and external cable 30 to the neurostimulation leads 12. The ETS 20, which has similar pulse generation circuitry as the IPG 14, also delivers electrical stimulation energy in the form of a pulse electrical waveform to the electrode array 26 in accordance with a set of stimulation parameters. The major difference between the ETS 20 and the IPG 14 is that the ETS 20 is a non-implantable device that is used on a trial basis after the neurostimulation leads 12 have been implanted and prior to implantation of the IPG 14, to test the responsiveness of the stimulation that is to be provided. Thus, any functions described herein with respect to the IPG 14 can likewise be performed with respect to the ETS 20.

The RC 16 may be used to telemetrically control the ETS 20 via a bi-directional RF communications link 32. Once the IPG 14 and neurostimulation leads 12 are implanted, the RC 16 may be used to telemetrically control the IPG 14 via a bi-directional RF communications link 34. Such control allows the IPG 14 to be turned on or off and to be programmed with different stimulation parameter sets. The IPG 14 may also be operated to modify the programmed stimulation parameters to actively control the characteristics of the electrical stimulation energy output by the IPG 14. As will be described in further detail below, the CP 18 provides clinician detailed stimulation parameters for programming the IPG 14 and ETS 20 in the operating room and in follow-up sessions.

The CP 18 may perform this function by indirectly communicating with the IPG 14 or ETS 20, through the RC 16, via an IR communications link 36. Alternatively, the CP 18 may directly communicate with the IPG 14 or ETS 20 via an RF communications link (not shown). The clinician detailed stimulation parameters provided by the CP 18 are also used to program the RC 16, so that the stimulation parameters can be subsequently modified by operation of the RC 16 in a stand-alone mode (i.e., without the assistance of the CP 18). The external charger 22 may also communicate with the IPG 14 via a communications link 38.

For purposes of brevity, the details of the RC 16, CP 18, ETS 20, and external charger 22 will not be described herein. Details of exemplary embodiments of these devices are disclosed in U.S. Pat. No. 6,895,280, which is expressly incorporated herein by reference.

Figure 2:
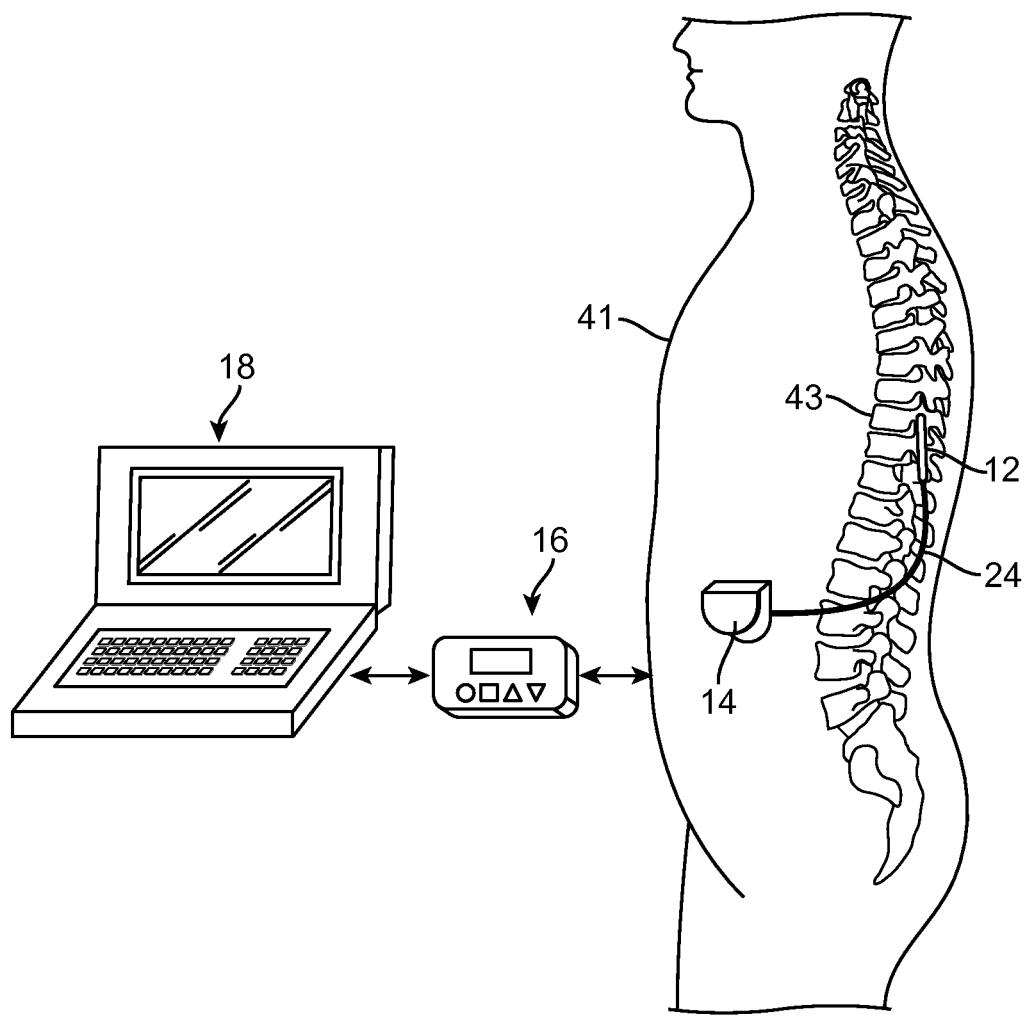
FIG. 2 is a plan view of the SCS system of FIG. 1 in use within a patient.

As shown in FIG. 2, the stimulation leads 12 are implanted within the spinal column 43 of a patient 41. The preferred placement of the stimulation leads 12 is adjacent to (e.g., in the epidural space), the spinal cord area to be stimulated. Due to the lack of space near the location where the stimulation leads 12 exit the spinal column 43, the IPG 14 is generally implanted in a surgically-made pocket either in the abdomen or above the buttocks. The IPG 14 may, of course, also be implanted in other locations of the patient's body. The lead extensions 24 facilitate locating the IPG 14 away from the exit point of the stimulation leads 12. As there shown, the CP 18 communicates with the IPG 14 via the RC 16.

Figure 3:
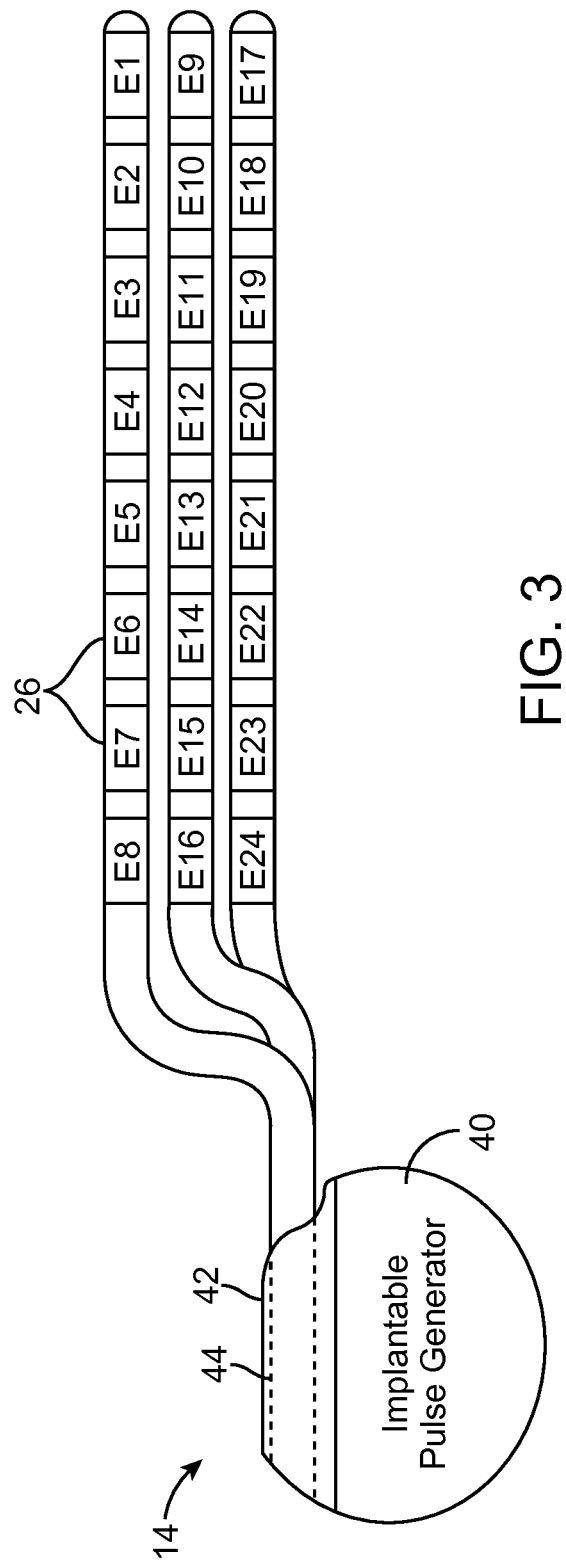
FIG. 3 is a plan view of an implantable pulse generator (IPG) and three percutaneous stimulation leads used in the SCS system of FIG. 1.

Referring now to FIG. 3, the external features of the stimulation leads 12 and the IPG 14 will be briefly described. Each of the stimulation leads 12 has eight electrodes 26 (respectively labeled E1-E8, E9-E16, and E17-E24). The actual number and shape of leads 12 and electrodes 26 will, of course, vary according to the intended application. Further details describing the construction and method of manufacturing percutaneous stimulation leads are disclosed in U.S. patent application Ser. No. 11/689,918, entitled "Lead Assembly and Method of Making Same," and U.S. patent application Ser. No. 11/565,547, entitled "Cylindrical Multi-Contact Electrode Lead for Neural Stimulation and Method of Making Same," the disclosures of which are expressly incorporated herein by reference.

Figure 4:
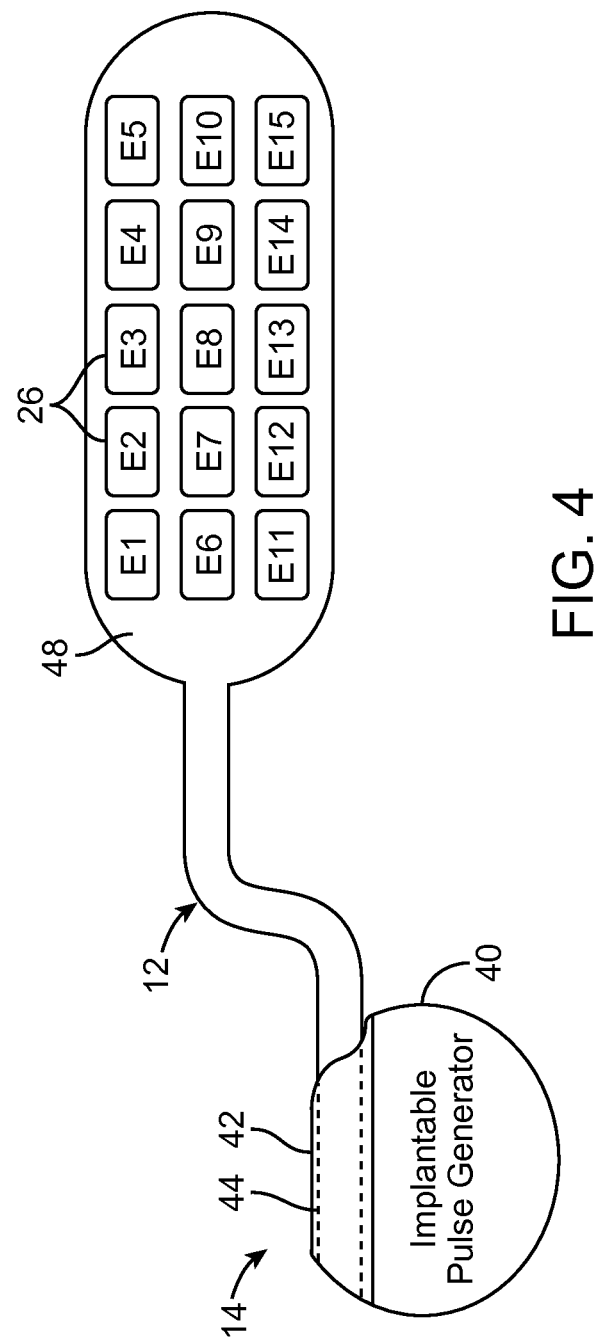
FIG. 4 is a plan view of an implantable pulse generator (IPG) and a surgical paddle lead used in the SCS system of FIG. 1.

Alternatively, as illustrated in FIG. 4, the stimulation lead 12 takes the form of a surgical paddle lead 48 on which electrodes 26 are arranged in a two-dimensional array in three columns (respectively labeled E1-E5, E6-E10, and E11-E15) along the axis of the stimulation lead 12. In the illustrated embodiment, five rows of electrodes 26 are provided, although any number of rows of electrodes 26 can be used. Each row of the electrodes 26 is arranged in a line transversely to the axis of the stimulation lead 12. The actual number of leads and electrodes will, of course, vary according to the intended application. Further details regarding the construction and method of manufacture of surgical paddle leads are disclosed in U.S. patent application Ser. No. 11/319,291, entitled "Stimulator Leads and Methods for Lead Fabrication," the disclosure of which is expressly incorporated herein by reference.

In each of the embodiments illustrated in FIGS. 3 and 4, the IPG 14 includes an outer case 40 for housing the electronic and other components (described in further detail below). The outer case 40 is composed of an electrically conductive, biocompatible material, such as titanium, and forms a hermetically sealed compartment, wherein the internal electronics are protected from the body tissue and fluids. In some cases, the outer case 40 may serve as an electrode. The IPG 14 further comprises a connector 42 to which the proximal ends of the stimulation leads 12 mate in a manner that electrically couples the electrodes 26 to the internal electronics (described in further detail below) within the outer case 40. To this end, the connector 42 includes one or more ports (three ports 44 or three percutaneous leads or one port for the surgical paddle lead) for receiving the proximal end(s) of the stimulation lead(s) 12. In the case, where the lead extensions 24 are used, the port(s) 44 may instead receive the proximal ends of such lead extensions 24.

The IPG 14 includes pulse generation circuitry that provides electrical conditioning and stimulation energy in the form of a pulsed electrical waveform to the electrode array 26 in accordance with a set of stimulation parameters programmed into the IPG 14. Such stimulation parameters may comprise electrode combinations, which define the electrodes that are activated as anodes (positive), cathodes (negative), and turned off (zero), percentage of stimulation energy assigned to each electrode (fractionalized electrode configurations), and electrical pulse parameters, which define the pulse amplitude (measured in milliamps or volts depending on whether the IPG 14 supplies constant current or constant voltage to the electrode array 26), pulse width (measured in microseconds), pulse rate (measured in pulses per second), and burst rate (measured as the stimulation on duration X and stimulation off duration Y).

Electrical stimulation will occur between two (or more) activated electrodes, one of which may be the IPG case 40. Simulation energy may be transmitted to the tissue in a monopolar or multipolar (e.g., bipolar, tripolar, etc.) fashion. Monopolar stimulation occurs when a selected one of the lead electrodes 26 is activated along with the case 40 of the IPG 14, so that stimulation energy is transmitted between the selected electrode 26 and the case 40. Bipolar stimulation occurs when two of the lead electrodes 26 are activated as anode and cathode, so that stimulation energy is transmitted between the selected electrodes 26. For example, an electrode on one stimulation lead 12 may be activated as an anode at the same time that an electrode on the same lead or another stimulation lead 12 is activated as a cathode. Tripolar stimulation occurs when three of the lead electrodes 26 are activated, two as anodes and the remaining one as a cathode, or two as cathodes and the remaining one as an anode. For example, two electrodes on one stimulation lead 12 may be activated as anodes at the same time that an electrode on another stimulation lead 12 is activated as a cathode.

The stimulation energy may be delivered between electrodes as monophasic electrical energy or multiphasic electrical energy. Monophasic electrical energy includes a series of pulses that are either all positive (anodic) or all negative (cathodic). Multiphasic electrical energy includes a series of pulses that alternate between positive and negative. For example, multiphasic electrical energy may include a series of biphasic pulses, with each biphasic pulse including a cathodic (negative) stimulation pulse and an anodic (positive) recharge pulse that is generated after the stimulation pulse to prevent direct current charge transfer through the tissue, thereby avoiding electrode degradation and cell trauma. That is, charge is conveyed through the electrode-tissue interface via current at an electrode during a stimulation period (the length of the stimulation pulse), and then pulled back off the electrode-tissue interface via an oppositely polarized current at the same electrode during a recharge period (the length of the recharge pulse).

Figure 5A:
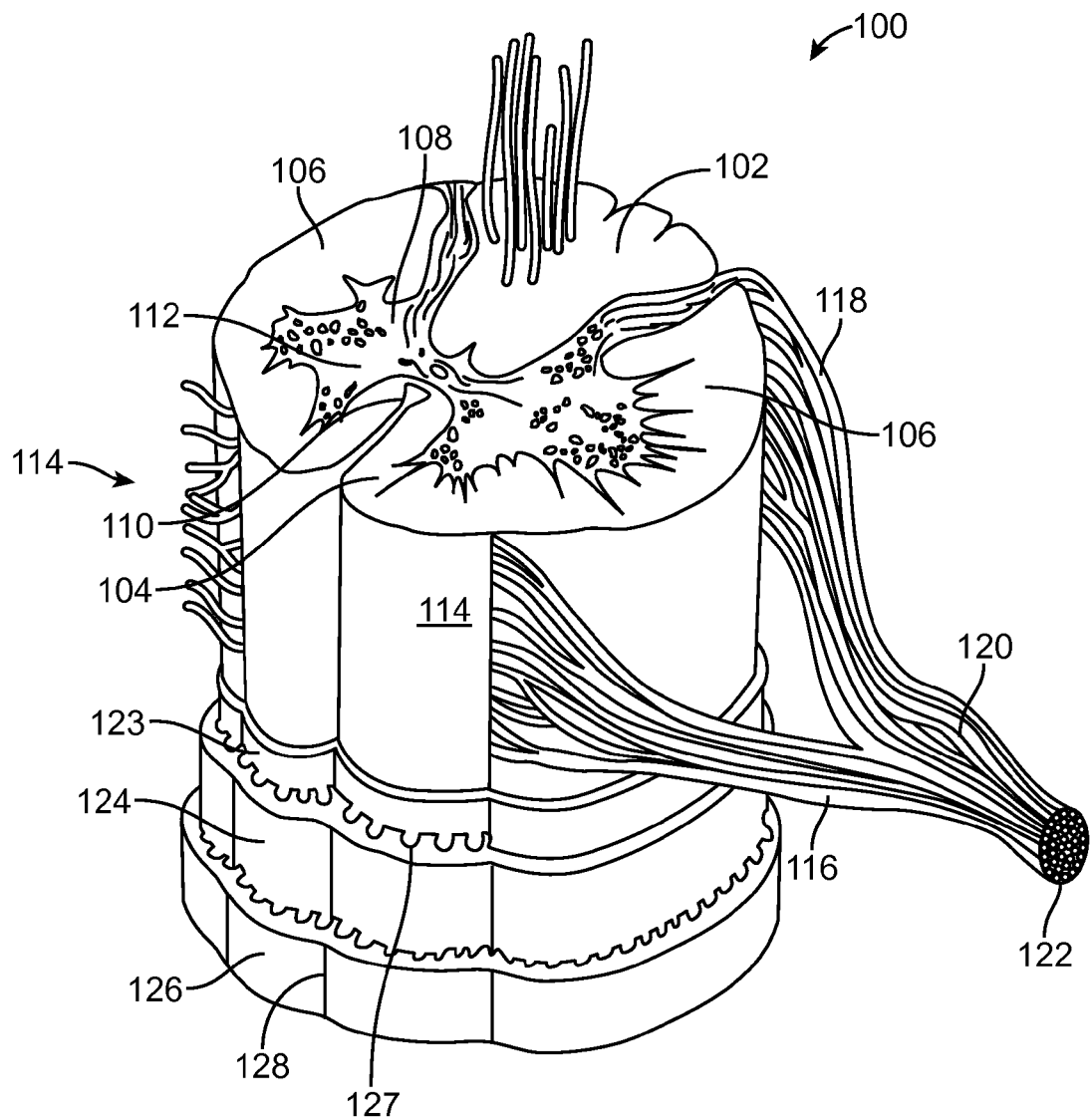
FIG. 5A is a pictorial view of the spinal cord and spinal nerves.
Figure 5B:
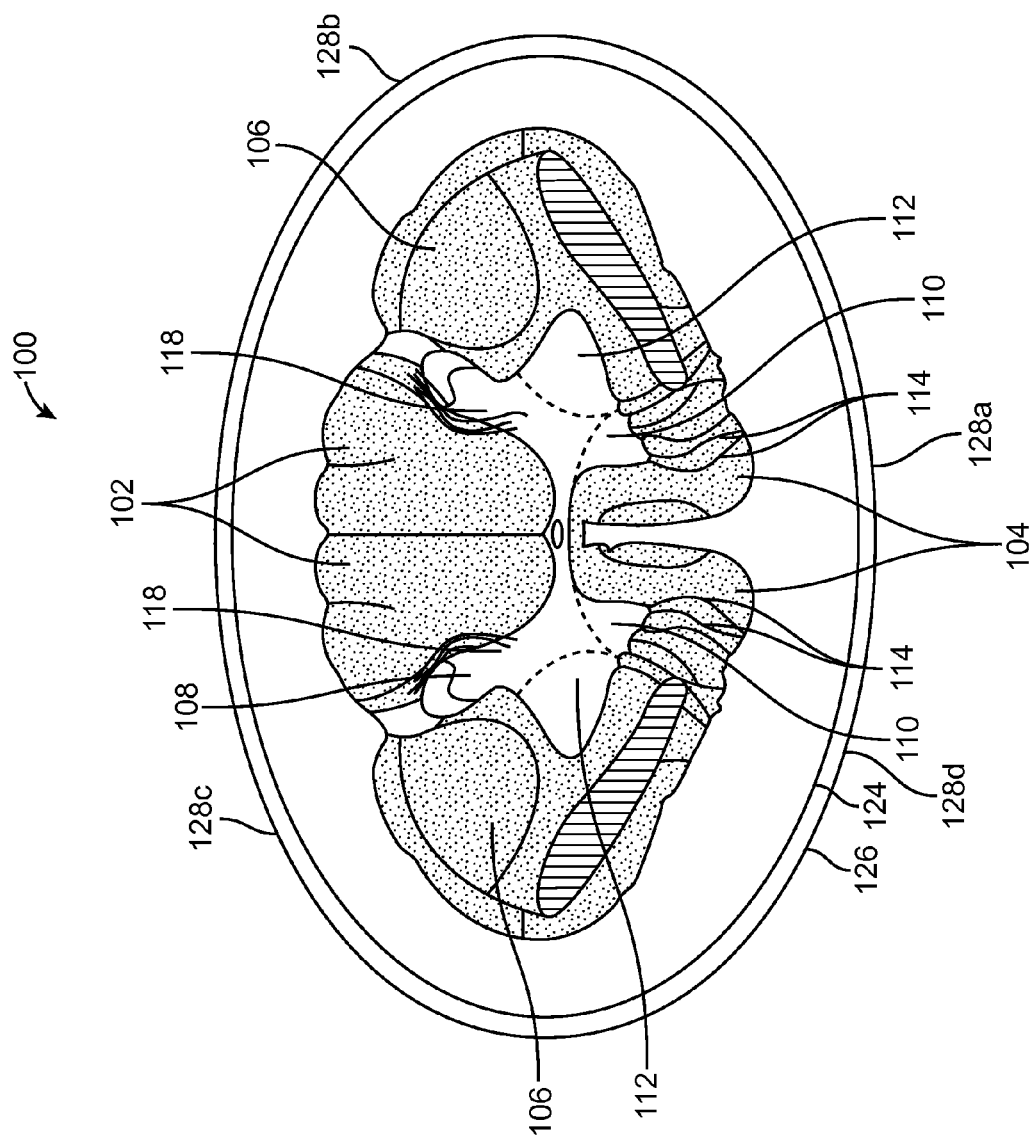
FIG. 5B is a sectional view of the spinal cord.
Figure 6:
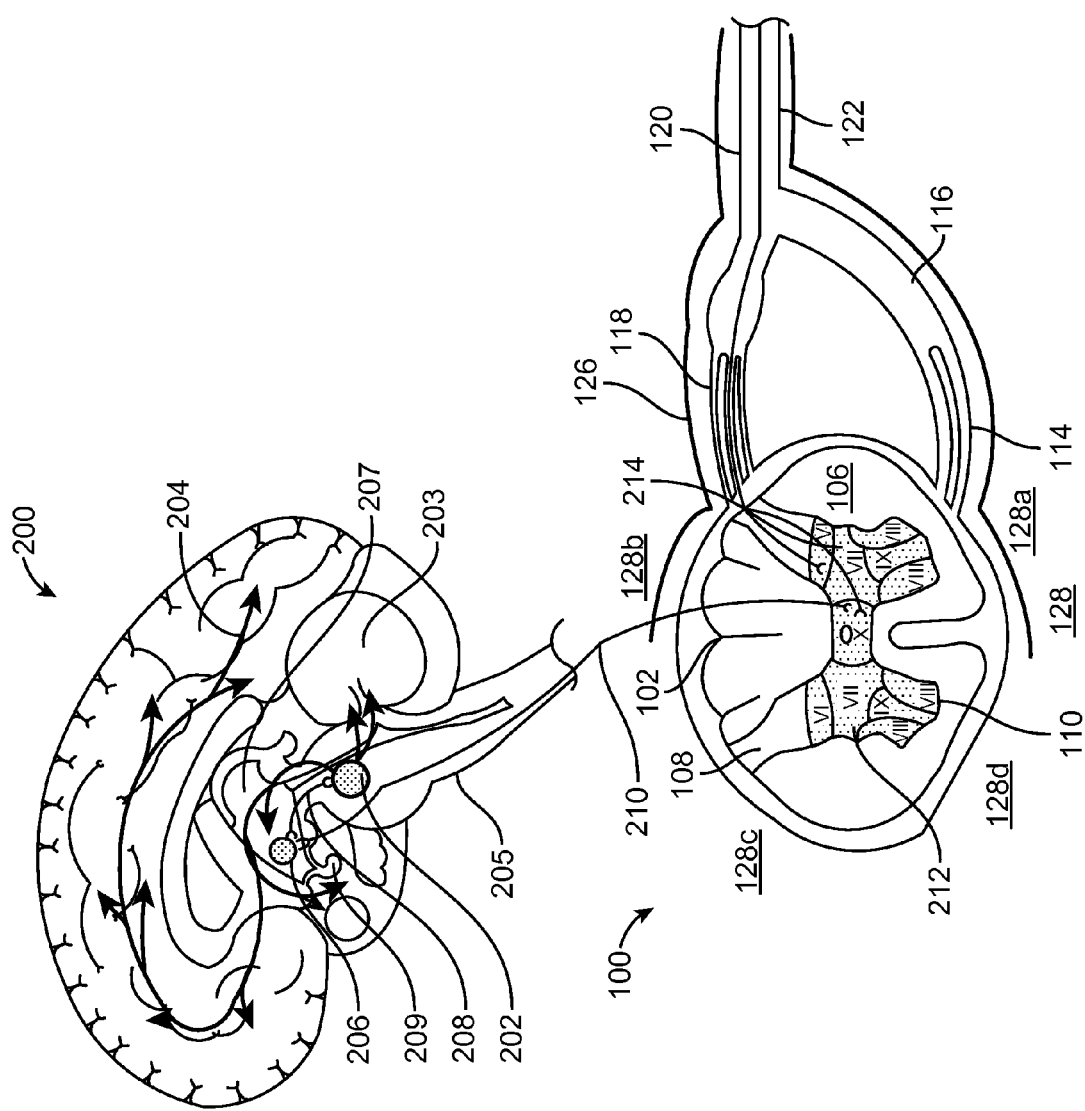
FIG. 6 is a schematic diagram depicting the afferent pathway connecting the sacral spinal cord, the hypothalamus, and the raphe nuclei.

Referring now to FIGS. 5A, 5B, and 6, the portions of the spinal cord 100 that are relevant to the present inventions will be described. The spinal cord 100 is divided into three columns: the dorsal column (DC) 102, the ventral column (VC) 104, and the lateral columns 106. One lateral column lies on either side of the spinal cord 100. Similarly, the butterfly-shaped gray matter of the spinal cord 100 is divided into the dorsal horn 108, the ventral horn 110, and the lateral horn 112. A ventral median fissure 109 divides the spinal cord 100 into two lateral halves.

A group of motor nerve rootlets (ventral root nerve fibers) 114 branch off of the ventral horn 110 and combine to form the ventral root (VR) 116. Similarly, a group of sensory nerve rootlets (dorsal root (DR) nerve fibers) 118 branch off of the dorsal horn 108 and combine to form the dorsal root 120. The dorsal root 120 and the ventral root 116 combine to form the spinal nerve 122, which innervates peripheral regions (e.g., arms, legs, etc.) of the patient's body. It will be noted that symmetrical motor nerve rootlets, ventral root, sensory nerve rootlets, dorsal root, and spinal nerve are located on the opposite side of spinal cord 100, but these elements are omitted for simplicity. A number of spinal nerves branch off the spinal cord. The spinal cord 100 is protected by three layers of connective tissue, the dura mater 126, the arachnoid 124, and the pia mater 123, collectively referred to as meninges. In the interest of simplicity, the dura 126 is shown in FIG. 6 only on the right side of the spinal cord 100. It will be understood that the illustrated structure is repeated on the left side of the spinal cord 100. Epidural space 128 surrounds the dura mater 126, and subarachnoid space 127 lies under the arachnoid 124. The epidural space 128 may be topologically divided into four quadrants: a right ventral-lateral quadrant 128a, a right dorsal-lateral quadrant 128b, a left dorsal-lateral quadrant 128c, and a left ventral-lateral quadrant 128d.

Referring now to FIG. 6, an afferent pathway connecting the sacral spinal cord 100, the hypothalamus 206, and the raphe nuclei 202 will be described. The raphe nuclei 202 are a moderate-size cluster of nuclei found in the brain stem. Many of the raphe nuclei 202 contain serotonergic neurons, which synthesize serotonin (5-hydroxytryptamine (5-HT)), a monoamine transmitter generally associated with mood disorders such as depression. Axons 204 extending from the raphe nuclei 202 form a neurotransmitter system reaching almost every part of the central nervous system. Such axons in lower raphe nuclei 202 terminate in the cerebellum 203 and spinal cord 100, while axons of the higher nuclei 202 spread out in the brain 200. Conventional pharmacology attempts to treat depression with selective serotonin re-uptake inhibitors (SSRIs), which may target the raphe nuclei 202 in a manner that results in a release of serotonin. The hypothalamus 206, located between the brain stem 205 and the thalamus 207, performs a variety of functions, including linking the nervous system to the endocrine system via the pituitary gland 209. In addition, it controls several metabolic processes and other activities of the autonomic nervous system. A group of small nuclei within the hypothalamus 206 mediate actions in coordination with the raphe nuclei 202. For example, neurons 208 carry afferent inputs to raphe nuclei 202 from the hypothalamus 206.

It recently has been found that the sacral portion of the spinal cord projects directly to the medial preoptic area in the hypothalamus 206 (See Klop E M, Kuipers R, Mouton L J. Neuroscience 2009 Dec. 29; 164(4): 1732-43). That connection traces to laminae VI-X (shown as 212) of the sacral spinal cord 100. Thus, a pathway exists from the sacral spinal nerve 122, through dorsal rootlets 118, to the sacral portion of spinal cord 100, the hypothalamus 108 to raphe nuclei 202.

Embodiments of the present invention take advantage of the pathway described above to stimulate raphe nuclei 202. In general, embodiments of the present invention apply electrical stimulation energy to afferent nerve fibers leading to the medial preoptic region of the hypothalamus 206 of the patient, thereby activating serotonin in the raphe nuclei 202 to treat depression. Various methods may be used to achieve this end. For example, afferent nerve fibers 214 lie within the dorsal root 120 of the sacral spinal nerves S1, S2, and S3 that connect to the laminae VI-X 212. Stimulating the dorsal root 120 stimulates afferents 214, which in turn stimulates nerve fiber 210. That nerve, which leads to the medial preoptic region of the hypothalamus of the patient, further stimulates hypothalamus 206, and consequently, raphe nuclei 202. At the end of this pathway, the stimulated raphe nuclei 202 release serotonin, which ameliorates the patient's depression or mood swings.

Figure 7:
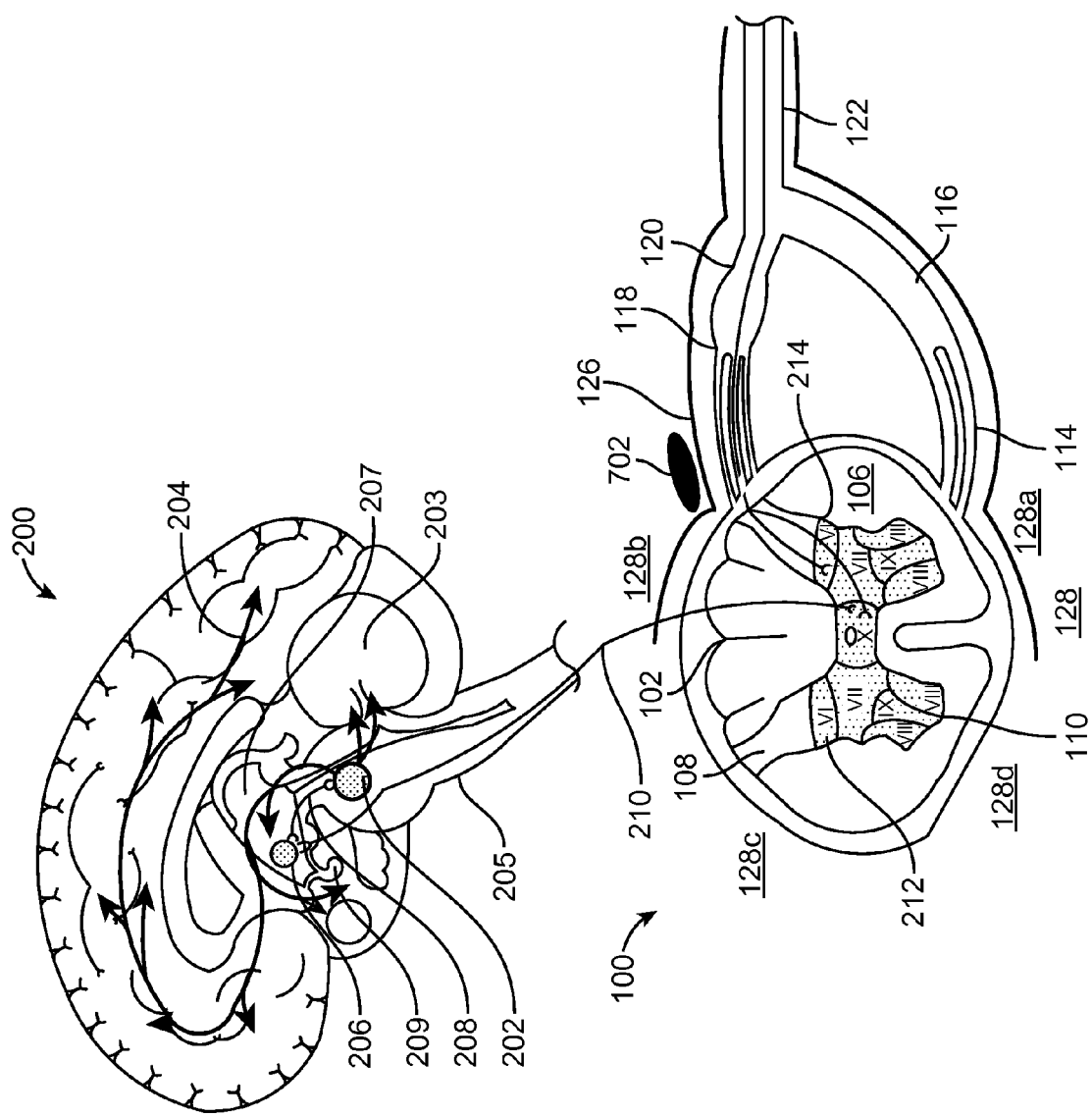
FIG. 7 is a schematic view showing a single-electrode arrangement relative to the spinal cord and spinal nerves, having afferents projecting to the raphe nuclei in the brain, in accordance with a first stimulation regime of the present invention.

Referring to FIG. 7, an exemplary embodiment of the present invention will be described, in which an electrode 702 may be implanted in the right dorsal-lateral epidural space 128b. The electrode 702 can be single electrode or an electrode array, or any of the forms of electrodes 26 discussed above. The location and stimulation regime associated with the electrode 702 may be designed to stimulate \afferent neural structures, such as, for example, dorsal rootlets 118, and/or dorsal root 120 of sacral spinal nerve S1, S2, or S3. In this context, stimulation is defined as stimulation sufficient to engender synthesis of serotonin within the raphe nuclei 202, which may reduce depression and other mood disorders within a patient. For treatment of depression, optimal locations are generally near the dorsal roots 120 of the spinal nerves S1, S2, and S3. However, a person of average skill in the art may contemplate other locations appropriate to position the electrode 702.

In the illustrated embodiment, the stimulation may be delivered by a train of electrical pulses at a rate between 2 Hz and 10 KHz, with a pulse width between 20 μs and 2000 μs. The amplitude of stimulating current may lie between 0.1 mA and 20 mA. Stimulation times can be varied and can be programmed for delivery in bursts, or the stimulation can be continuously applied for a set period of time. Although these parameter ranges may engender serotonin synthesis, a set of parameters appropriate for a particular patient may differ from others. A physician may calibrate appropriate parameters according to specific needs of a patient.

The embodiments set out above all illustrate electrodes implanted on one side of a spinal column 100, on a single spinal level. Depending on a patient's needs, multiple electrodes can be implanted, occupying sites on both sides of the spinal column and on multiple spinal levels. These and other variations in the recited embodiments will be clear to those of skill in the art.

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

What is claimed is:

1. A method for treating a patient suffering from depression, the method comprising:
   applying electrical stimulation energy from at least one electrode configured for implantation within the epidural space of the patient, to afferent nerve fibers leading to the medial preoptic region of the hypothalamus of the patient, thereby activating serotonin in the raphe nuclei to treat depression, wherein the afferent nerve fibers are at a sacral spinal level in the range of S1-S3.

2. The method of claim 1, wherein the electrical stimulation energy is epidurally applied to the afferent nerve fibers.

3. The method of claim 1, wherein the afferent nerve fibers are a dorsal root (DR).

4. The method of claim 1, wherein the at least one electrode is configured for implantation within the dorsal-lateral quadrant of an epidural space of the patient.

5. The method of claim 1, wherein the afferent nerve fibers are within laminae VI-X of the spinal cord.

* * * * *